United States Patent [19]

Fujita et al.

[11] 4,025,539

[45] * May 24, 1977

[54] PROCESS FOR PREPARING 2-SUBSTITUTED OR UNSUBSTITUTED GERANYL ACETIC ACIDS AND ESTERS THEREOF

[75] Inventors: Yoshiji Fujita, Kurashiki; Yoshiaki Omura, Okayama; Takashi Nishida; Kazuo Itoi, both of Kurashiki, all of Japan

[73] Assignee: Kuraray Co., Ltd., Kurashiki, Japan

[*] Notice: The portion of the term of this patent subsequent to Dec. 23, 1992, has been disclaimed.

[22] Filed: Nov. 20, 1975

[21] Appl. No.: 633,612

[30] Foreign Application Priority Data

Nov. 21, 1974 Japan .............................. 49-134801

[52] U.S. Cl. .................. 260/404; 260/404.5; 260/410; 260/410.9 R; 260/410.9 N
[51] Int. Cl.² ...................... C09F 5/00; C09F 3/02
[58] Field of Search ............ 260/410.9 R, 410, 413, 260/404, 404.5, 410.9 N

[56] References Cited

UNITED STATES PATENTS

| | | | |
|---|---|---|---|
| 2,848,502 | 8/1958 | Surmatis | 260/631.5 |
| 3,154,570 | 10/1964 | Adami et al. | 260/410.9 R |
| 3,928,403 | 12/1975 | Fujita et al. | 260/410.9 R |

Primary Examiner—Winston A. Douglas
Assistant Examiner—John F. Niebling
Attorney, Agent, or Firm—Bacon & Thomas

[57] ABSTRACT

2-substituted or unsubstituted geranyl actic acid esters represented by the general formula [I],

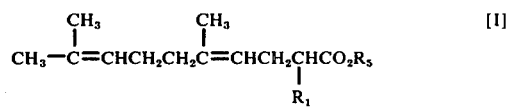

wherein $R_1$ represents a hydrogen atom or a hydrocarbon and $R_5$ is the same as $R_2$, $R_3$ or $R_4$ hereinafter defined, are prepared by reacting linalool (II) with 2-substituted or unsubstituted ortho acetic acid ester derivatives represented by the general formula [III]

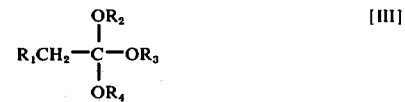

wherein $R_2$, $R_3$ and $R_4$, which are the same or different, each represents an alkyl group or a cycloalkyl group, in the presence of an acidic catalyst.

10 Claims, No Drawings

PROCESS FOR PREPARING 2-SUBSTITUTED OR UNSUBSTITUTED GERANYL ACETIC ACIDS AND ESTERS THEREOF

BACKGROUND OF THE INVENTION

1. Field of the Invention

The present invention relates to a process for preparing 2-substituted or unsubstituted geranyl acetic acids or esters thereof which are especially useful as pharmaceuticals in the treatment or prophylaxis of dermatosis, such as acne, psoriasis, decubital ulcers or verruca. (See, e.g., British Pat. No. 1,173,419 and Japanese Patent Publication No. 49-43917 corresponding to U.S. patent application Ser. No. 271,687, filed July 14, 1972 now abandoned).

2. Description of the Prior Art 2-substituted geranyl acetic acids or esters have heretofore been prepared by the following processes.

1. 2-cyclohexyl geranyl acetic acid by the combination of the steps of reacting citral with ethyl cyanoacetate to give the condensation product, reducing the condensation product with sodium borohydride to give ethyl geranyl cyanoacetate, alkylating the geranyl cyanoacetate with cyclohexyl bromide in the presence of alkali and then subjecting said product to hydrolysis with alkali, such as potassium hydroxide, decarboxylation and neutralization to give the product.
2. A process for preparing 2-cyclohexyl geranyl acetic acid by the combination of the steps of reacting cyclohexanone with ethyl cyanoacetate to give the condensation product, reducing said product with sodium borohydride to give ethyl cyclohexyl cyanoacetate, reacting said ethyl cyclohexyl cyanoacetate with geranyl chloride and then subjecting the product thus obtained to hydrolysis, decarboxylation and neutralization to give the product.
3. 2-cyclohexyl geranyl acetic acid has also been prepared by reacting cyclohexyl bromide or geranyl chloride with ethyl cyanoacetate to give the condensation product, reacting further cyclohexyl bromide or geranyl chloride with the condensation product, and then subjecting the product thus obtained, to hydrolysis, decarboxylation and neutralization to give the product.
4. A process for preparing 2-substituted geranyl acetic acid (2-substituted-5,9-dimethyl-4,8-decadienoic acid), for example, 2-cyclohexyl geranyl acetic acid by reacting linalool with substituted malonic ester, for example, cyclohexyl malonic ester with heating to give the ester of 2-substituted geranyl acetic acid and saponifying the ester with alkali to give the product.

The foregoing methods suffer from the disadvantages inherent in a multistage process and the fact that low yields of the desired product are obtained.

SUMMARY OF THE INVENTION

It is, therefore, a primary object of the present invention to provide a process for the preparation of 2-substituted or unsubstituted geranyl acetic acid esters which obviates the disadvantages and problems associated with prior art processes.

Another object of the present invention is to provide 2-substituted or unsubstituted geranyl acetic acid esters simply and economically in a single step and in excellent yields by reacting linalool with a 2-substituted or unsubstituted ortho acetic acid ester in the presence of an acidic catalyst.

These and other objects of the present invention are accomplished by the products and processes thereof comprising a process for the preparation of 2-substituted or unsubstituted geranyl acetic esters of the general formula

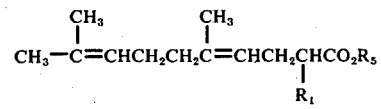

by a process comprising reacting linalool with a 2-substituted or unsubstituted ortho acetic acid ester derivative represented by the general formula

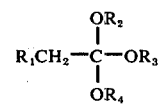

wherein $R_1$ represents a hydrogen atom, an alkyl group, a cycloalkyl group, an alkenyl group, a cycloalkenyl group, an alkynyl group or an aryl group and $R_2$, $R_3$ and $R_4$ are the same or different and represent an alkyl group or a cycloalkyl group, in the presence of an acidic catalyst.

Other objects, advantages and features of the present invention will become apparent to those skilled in the art from the detailed description which follows.

DETAILED DESCRIPTION OF THE INVENTION

In accordance with the present invention, 2-substituted or unsubstituted geranyl acetic acid esters of the above formula [I] may be effectively prepared in a single step and in excellent yield by the process of the present invention which comprises reacting linalool (3,7-dimethyl-1,6-octadien-3-ol) [II] with a 2-substituted or unsubstituted orthoacetic acid ester derivative represented by the general formula [III]

wherein $R_1$ represents a hydrogen atom, an alkyl group, a cycloalkyl group, an alkenyl group, a cycloalkenyl group, an alkynyl group or an aryl group; and $R_2$, $R_3$ and $R_4$, which are the same or different, each represents an alkyl group or a cycloalkyl group in the presence of an acidic catalyst.

Among the products produced by the present invention, 2-substituted geranyl acetic acid ester represented by the general formula

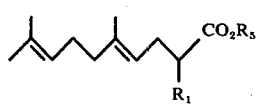

wherein $R_1$ represents a hydrocarbon radical of 1 to 20 carbon atoms, such as an alkyl group of 1 to 20 carbon atoms, a cycloalkyl group of 3 to 20 carbon atoms, an alkenyl group of 2 to 20 carbon atoms, a cycloalkenyl group of 3 to 20 carbon atoms, an alkynyl group of 2 to 20 carbon atoms or an aryl group of 6 to 20 carbon atoms and wherein $R_5$ represents one of $R_2$, $R_3$ or $R_4$ as defined in formula [III] are therapeutically useful compounds, especially as anti-ulcer agents, as described with respect to 2-substituted geranyl acetic acid in British Pat. No. 1,173,419. The compound 2-cyclohexyl geranyl acetate described hereinafter in Example 8 has been found to be a particularly advantageous anti-ulcer agent and can also be advantageously employed in the treatment of the aforementioned dermatosis conditions.

The 2-substituted or unsubstituted geranyl acetic acid esters produced by the process of the present invention are represented by the general formula

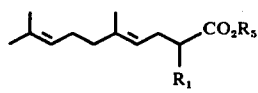

wherein $R_1$ is as defined in formula [III] and wherein $R_5$ represents one of $R_2$, $R_3$ and $R_4$ as defined in the formula [II].

More specifically, $R_1$ may be a hydrogen atom, an alkyl group of 1 to 20 carbon atoms, e.g. methyl, ethyl, propyl, butyl, amyl, decyl, pentadecyl, eicosyl, etc.; a cycloalkyl group of 3 to 20 carbon atoms, e.g. cyclohexyl, cycloheptyl, cyclodecyl, etc.; an alkenyl group of 2 to 20 carbon atoms, e.g. vinyl, allyl, pentenyl, octenyl, decenyl, nonadecenyl, etc.; a cycloalkenyl group of 30 to 20 carbon atoms, e.g. 1-cyclohexenyl, etc., an alkynyl group of 2 to 20 carbon atoms, e.g. ethynyl, proynyl, hexynyl, decynyl, etc. or an aryl group of 6 to 20 carbon atoms, e.g. phenyl naphthyl, etc.

Furthermore, $R_1$ may be a substituted hydrocarbon group of 1 to 20 carbon atoms wherein the substituent is, e.g., an amino-group, dialkyl amino-group, dialkenyl amino-group, or piperazino-group the alkyl or alkenyl group of said substituent being comprised of 1 to 6 carbon atoms.

$R_2$, $R_3$ and $R_4$ may be the same or different and each represents an alkyl group of 1 to 8 carbon atoms such as methyl, ethyl, n-propyl, isopropyl, n-butyl, t-butyl, pentyl, hexyl, heptyl, octyl, or a cycloalkyl group of 3 to 8 carbon atoms, e.g. cyclopropyl, cyclohexyl, cyclooctyl, etc.

$R_1$, $R_2$, $R_3$ and $R_4$ each may have a total number of carbon atoms outside of the above ranges. Broadly $R_1$ may be a hydrogen atom or any hydrocarbon group having from 1 to 20 carbon atoms, including those groups above-mentioned and also including aralkyl or alkaryl groups.

Typical examples of the compound III which may be used in the practice of the present invention are 1,1,1-trimethoxyethane, 1,1,1-triethoxyethane; 1,1,1-tripropoxy ethane; 1,1,1-tricyclohexyloxyethane; 1,1,1-tri-(n-butoxy) ethane; 1,1,1-trimethoxy propane; 1,1,1-triethoxy propane; 1,1-dimethoxy-1-cyclohexyloxy ethane; 1,1,1-triethoxy butane 1,1,1-triethoxy-2-cyclohexyl ethane; 1,1,1-triethoxy butane; 1,1,1-triethoxy-2-cyclohexyl ethane; 1,1,1-triethoxy-2-phenylethane; 1,1,1-triethoxy-4-N,N-dimethylamino-butane; 1,1,1-triethoxy-4-N,N-diprenylamino-butane; 1,1,1-triethoxy-4-N-methylpiperazino-butane and the like.

The acidic catalyst may be any conventional acid catalyst and is used generally in a conventional amount, e.g. about 0.1 to 2%, preferably 1 to 10%, based on the weight of the starting linalool. Examples of suitable acidic catalysts are lower fatty acids, e.g. acetic acid, propionic acid, butyric acid, isobutyric acid, valeric acid, malonic acid, succinic acid, adipic acid etc.; sulfonic acids, e.g. p-toluenesulfonic acid, benzene sulfonic acid, etc., mineral acids, e.g. hydrochloric acid, sulfuric acid, phosphoric acid, etc.; and Lewis acids such as zinc chloride, ferrous chloride, boron trifluoride, aluminum chloride, etc.; phenols e.g. phenol, o-, m- or p-cresol, o, m, or p-nitrophenol and hydroquinones.

A solvent is not necessary in the reaction but inert solvents such as n-heptane, n-octane, benzene, toluene, o-, m-or p-xylene may be used. Alternatively, 2-substituted orthoacetic acid esters may be used in excess to comprise the solvent.

The molar ratio of linalool to 2-substituted orthoacetic acid esters may be anywhere within the range of 1/1.1 to 1/4 and the excess of orthoacetic acid esters, if any, recovered economically.

The reaction may be effected at 50 to 200° C, preferably 120° to 170° C taking into account the desired reaction rate and selectively, although the temperature is not critical and may vary outside of these ranges.

The duration of the reaction is not critical and may vary from 30 minutes to 40 hours.

It is preferred that the alcohol which is formed as a by-product be removed during the reaction by distillation. The product geranyl acetic acid ester may be recovered by first removing low boiling components from the reaction mixture, such as the catalyst and any unreacted 2-substituted orthoacetic acid ester, and distilling the residue.

2-substituted or unsubstituted geranyl acetic acid may be obtained by conventional saponification of the corresponding 2-substituted or unsubstituted gernayl acetate obtained by the process of the present invention. A suitable saponification catalyst and the saponification conditions of said geranyl acetate may be the same as those described in British Pat. No. 1,173,419.

The following examples are intended to illustrate the invention as applied to representative products and are further for the purpose of illustrating the best mode contemplated for carrying out the invention and to supplement the foregoing disclosure of the invention with additional descriptions of the manner and process of carrying out the invention so as further to enable those skilled in the art to do so.

EXAMPLE 1

154 grams of linalool (3.7-dimethyl-1,6-octadien-3-ol), 324 g of 1,1,1-triethoxy ethane and 4.6 g of butyric acid are placed in a three-necked flask having 500 ml of inner capacity, and reacted for 8 hours with stirring under heating at 140° to 145° C and with removal of ethanol formed during the reaction. The liquid reaction product is directly distilled to remove the low boiling material such as butyric acid, whereby the unreacted 1,1,1-triethoxy ethane is recovered. The residue is distilled under high vacuum to give the ethyl geranyl acetate as a distillate boiling at 120° to 122° C/3.3 mm Hg. The yield is 92.6%.

The distillate thus obtained was identified by mass spectrometry and nuclear magnetic reasonance (NMR spectrum).

The distillate exhibited molecular ion peaks of [M+] = 224 by mass spectrometry.

The distillate exhibited the following δ-values (ppm) of NMR spectrum in a solution of tetrachlorocarbon.

1.15 (3H, t); 1.52 and 1.60 (9H, s); ca. 195 and 2.15 (8H, m); 4.02 (2H, q); 5.05 (2H, s).

The elementary analysis values of the distillate is as follows:

Calculated: C = 75.00%, H = 10.71%, O = 14.28%.
Found: C = 74.76%, H = 10.68%, O = 14.52%.

EXAMPLE 2

154 grams of linalool, 352 g of 1,1,-triethoxy propane and 4.6 g of butyric acid are placed in a three-necked flask having a 1000 ml capacity, and reacted for 6 hours with stirring under heating at 150° to 155° C and with removal of ethanol formed during the reaction in the same manner described in Example 1. The liquid reaction product is distilled to give 214 g of ethyl 2-methyl geranyl acetate.

Ethyl 2-methyl geranyl acetate thus obtained was identified by mass spectrometry and NMR spectrum.

The distillate exhibited molecular ion peaks of [M+] = 238 by mass spectrometry.

The distillate exhibited the following δ-values (ppm) of NMR spectrum in a solution of tetrachlorocarbon.

1.18 (6H, t); 1.54 (3H, s); 1.60 and 1.65 (6H, s); 1.93 (4H, m); 2.93 (1H, dt); 4.06 (2H, q); 5.10 (2H, m).

EXAMPLES 3 TO 10

These reactions are effected as in Example 1 except that various ortho-organic esters were used, as shown in the following table along with the results.

In the Table above, the chemical names of the products are as follows.

3. Ethyl geranyl acetate; 4. Propyl geranyl acetate; 5. n-Butyl geranyl acetate; 6. Ethyl 2-methyl geranyl acetate; 7. Ethyl 2-ethyl geranyl acetate; 8. Ethyl 2-cyclohexyl geranyl acetate; 9. Ethyl 2-phenyl geranyl acetate; and 10. Ethyl 2-dimethyl amino propyl geranyl acetate.

In the Table above, Et, Pr, $B_u^n$ and

stand for ethyl, n-propyl, n-butyl and cyclohexyl groups, respectively.

While the invention has been shown and described by reference to preferred embodiments thereof, it is to be expressly understood that various changes, modifications and/or substitutions may be made therein without departing from the spirit and scope thereof, it being the intention that the invention be limited only by the scope of the appended claims.

What is claimed is:

1. A process for preparing geranyl acetic acid esters of the formula [I]:

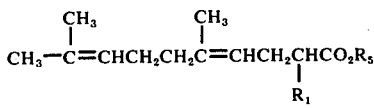

wherein $R_1$ represents a hydrogen atom or a hydrocarbon group of 1 to 20 carbon atoms, and $R_5$ is the same as $R_2$, $R_3$ or $R_4$ below in formula [III], said process comprises reacting linalool with a 2-substituted orthoacetic acid ester derivative of the formula [III]:

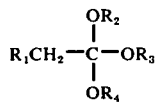

wherein $R_1$ is as defined in formula [I] above and $R_2$, $R_3$ and $R_4$, which may be the same or different, each represents an alkyl group of 1 to 8 carbon atoms or a cycloalkyl group of 3 to 8 carbon atoms; in the presence of an acidic catalyst.

2. The process of claim 1, wherein said $R_1$ is a hydrogen atom, an alkyl group of 1 to 20 carbon atoms, a cycloalkyl group of 3 to 20 carbon atoms, an alkenyl group of 2 to 20 carbon atoms, a cycloalkenyl group of 3 to 20 carbon atoms, an alkynyl group of 2 to 20 carbon atoms or an aryl group of 6 to 20 carbon atoms.

3. The process of claim 1, wherein the temperature of reaction is from about 50° and 200° C.

4. The process of claim 1, wherein the reaction is effectuated in a inert solvent.

5. The process of claim 1, wherein the said acidic catalyst is employed in an amount ranging between about 0.1 and 20% by weight, based on the weight of said linalool.

6. The process of claim 1, wherein said acidic catalyst is a weak acid.

7. The process of claim 1, wherein said acidic catalyst is a lower fatty acid, a sulfonic acid, mineral acid, a Lewis acid, a phenol compound or hydroquinone.

8. The process of claim 1, wherein said linolool and said 2-substituted or unsubstituted orthoacetic acid ester are employed in substantially equimolar amounts.

9. The process of claim 1, wherein the molar ratio of said linalool to said 2-substituted or unsubstituted orthoacetic acid ester is from 1/1.1 to 1/4.

10. The process of claim 1, wherein said 2-substituted or unsubstituted orthoacetic acid ester is selected from the group consisting of 1,1,1-trimethoxyethane, 1,1,1-triethoxyethane, 1,1,1-tripropoxyethane, 1,1,1-tricyclohexyloxy ethane, 1,1,1-tri(n-butoxy)ethane, 1,1,1-trimethoxy propane, 1,1,1-triethoxy propane, 1,1-dimethoxy-1-cyclohexyloxyethane, 1,1,1-triethoxybutane, 1,1,1-triethoxy-2-cyclohexylethane, 1,1,1-triethoxy-2-phenylethane, 1,1,1-triethoxy-4-N,N-dimethylamino-butane; 1,1,1-triethoxy-4-N,N-diphenylamino butane and 1,1,1-triethoxy-4-N-methyl-piperazino-butane.

* * * * *